United States Patent
Strohmaier et al.

(10) Patent No.: US 6,544,394 B1
(45) Date of Patent: Apr. 8, 2003

(54) SENSOR FOR ANALYZING GASES

(75) Inventors: Rainer Strohmaier, Stuttgart (DE); Carsten Springhorn, Stuttgart (DE); Detlef Heimann, Gerlingen (DE); Thomas Wahl, Pforzheim (DE); Margret Schuele, Weil der Stadt (DE); Bernd Schumann, Rutesheim (DE); Bernhard Bloemer, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/646,661
(22) PCT Filed: Jan. 15, 2000
(86) PCT No.: PCT/DE00/00135
§ 371 (c)(1),
(2), (4) Date: Nov. 30, 2000
(87) PCT Pub. No.: WO00/43767
PCT Pub. Date: Jul. 27, 2000

(30) Foreign Application Priority Data

Jan. 20, 1999 (DE) .......................................... 199 01 957

(51) Int. Cl.$^7$ ............................................. G01N 27/407
(52) U.S. Cl. ..................... 204/424; 204/428; 204/429; 73/23.31
(58) Field of Search ................................ 204/424, 425, 204/426, 427, 428, 429; 73/23.31, 23.32

(56) References Cited

U.S. PATENT DOCUMENTS

| | | | | |
|---|---|---|---|---|
| 4,741,817 A | * | 5/1988 | Croset et al. | 204/425 |
| 5,443,711 A | * | 8/1995 | Kojima et al. | 204/426 |
| 5,476,001 A | * | 12/1995 | Hoetzel et al. | 73/118.1 |
| 5,968,330 A | * | 10/1999 | Guth et al. | 204/421 |
| 6,379,514 B1 | * | 4/2002 | Schulte et al. | 204/424 |

FOREIGN PATENT DOCUMENTS

| | | |
|---|---|---|
| DE | 42 43 734 | 6/1994 |
| DE | 43 11 849 | 10/1994 |

* cited by examiner

*Primary Examiner*—Robert J. Warden, Sr.
*Assistant Examiner*—Kaj K. Olsen
(74) *Attorney, Agent, or Firm*—Kenyon & Kenyon

(57) ABSTRACT

A sensor for determining gas components and concentrations in a gas mixture that is particularly suitable for analyzing HC, $NO_x$ and CO in exhaust gases of internal combustion engines in the sensor, an outer electrode, that is separated from an $MO_x$ electrode by an electrolyte layer, is applied on a substrate. In this context, the outer electrode and the $MO_x$ electrode are in communication with the gas mixture to be analyzed. In addition, the outer electrode contains a region that is in contact with a gas-permeable tunnel layer which in turn contains a region that is directly exposed to the gas mixture to be analyzed, so that the gas to be analyzed can be supplied to the outer electrode via the gas-permeable tunnel layer.

14 Claims, 1 Drawing Sheet

SENSOR FOR ANALYZING GASES

BACKGROUND INFORMATION

The invention relates to a sensor for analyzing gases.

Such sensors are known in many forms. For example, reference is made to the German Published Patent Application No. 42 43 734 A1, and in particular to the German Published Patent Application No. 43 11 849 A1, which proposes a sensor in which an oxygen pump cell is provided with a solid electrolyte and a measuring element, the pump cell being connected to the measuring element by way of a porous diffusion layer, via which the oxygen pumped by the pump cell is conducted to the measuring element. In addition, the oxygen to be pumped is supplied to the solid electrolyte via at least one diffusion channel leading laterally to the porous solid electrolyte.

SUMMARY OF THE INVENTION

Compared to the related art, the gas sensor of the present invention has the advantage that signal stability is improved and signal generation is accelerated. Because the outer electrode in the hot region of the gas sensor is in contact at least region-wise with the gas-permeable tunnel layer, which is directly exposed region-wise to the gas mixture to be analyzed, the gas to be analyzed can be supplied quickly and directly in a very advantageous manner to the outer electrode via the gas-permeable tunnel layer. In particular, the outer electrode is exposed more directly, for example, to an exhaust gas to be analyzed, and the potential is adjusted more quickly and reliably.

In this context, one skilled in the art understands the hot region to be the region of the gas sensor which is exposed to the measuring gas or in which the measuring signal is formed, while to be understood by the cold region is the region of the electrode leads which is exposed to markedly lower temperatures and essentially does not contribute to the formation of the measuring signal.

It is also very advantageous if the gas-permeable tunnel layer covers the outer electrode at least to a great extent, and in particular, if the outer electrode covered by the tunnel layer is at the same time surrounded by the substrate and the electrolyte layer. Disposed advantageously on the electrolyte layer is the $MO_x$ electrode, so that on the one hand, this electrode is exposed directly to the gas to be analyzed, and on the other hand at least substantially covers the electrolyte layer.

To ensure that the gas to be analyzed has access that is as simple, quick and direct as possible to the outer electrode, which is preferably a Pt outer electrode, the tunnel layer also very advantageously has a gas-intake surface which is not covered by the electrolyte layer and/or the $MO_x$ electrode, and therefore has direct contact with the measuring gas.

Furthermore, because the gas-permeable tunnel layer and the electrolyte layer separate the outer electrode from the $MO_x$ electrode which, for example, is disposed above it, the electrolyte layer can now be virtually gas-tight or merely slightly porous. Without the gas-permeable tunnel layer of the present invention, till now it was absolutely requisite that the electrolyte layer be gas-permeable, so that the measuring gas to be analyzed could diffuse through the $MO_x$ electrode and the electrolyte layer to thus reach the outer electrode. However, at the same time, this involved the disadvantage that because of diffusion processes through the porous solid electrolyte layer, in the course of time the outer electrode could become contaminated by the $MO_x$ electrode. The gas-permeable tunnel layer of the present invention overcomes this disadvantage, and the structure of the solid electrolyte layer can now be optimized independently of the previous requirement for gas permeability.

Furthermore, for special applications it is advantageous if the gas-permeable tunnel layer is not, for example, designed as a self-supporting cavity, but rather merely exhibits a markedly greater open porosity compared to the electrolyte layer. This permits higher mechanical stability, better process compatibility and avoidance of deformation during sintering.

In particular, the tunnel layer can also be advantageously made of the same material as the electrolyte layer, and differ from it merely due to an increased open porosity.

In addition, if necessary, the tunnel layer can advantageously also be doped with a catalytically active material that, in particular, contains a noble metal, a noble-metal alloy or a transitional metal oxide such as a manganese oxide. This catalytically active material is introduced in particular into the pores of the tunnel layer, and preferably has the form of nano-scale colloids. By adding the catalytically active material, a pre-catalysis of an exhaust gas to be analyzed is advantageously attained, and thus an even faster and better equilibrium adjustment.

Moreover, the tunnel layer can also be advantageously formed as a diffusion barrier which is permeable to specific gases, so that unwanted gas components from the measuring gas to be analyzed cannot reach the outer electrode.

Incidentally, the size of the tunnel layer is advantageously selected so that it is not covered by the electrolyte layer and the $MO_x$ electrode toward the cold side of the gas sensor.

DETAILED DESCRIPTION

Figure 1:
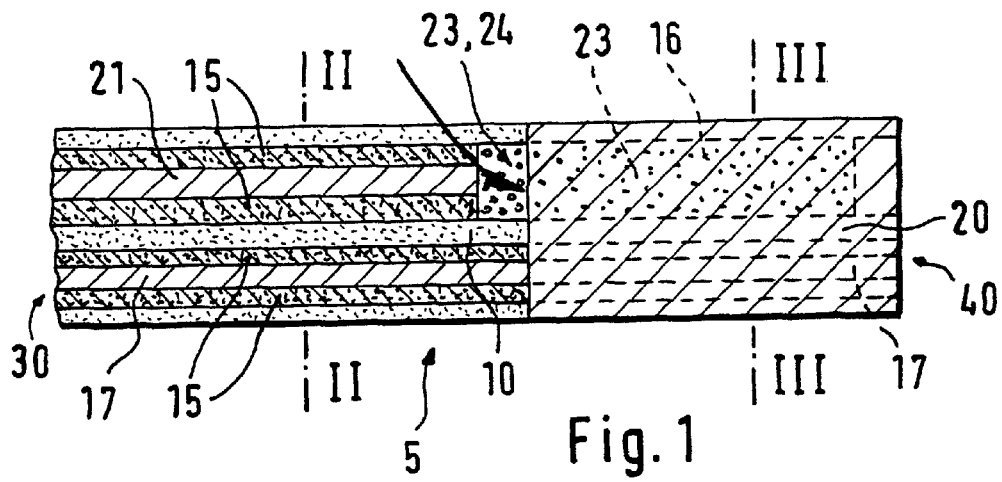
FIG. 1 shows a plan view of a sensor for analyzing gases according to the present invention.

FIG. 1 shows a plan view of a gas sensor 5 having a hot region 40 and a cold region 30. Running on a substrate made of $ZrO_2$ in cold region 30 are two strip-shaped, electrically isolating insulation layers 15 made of $Al_2O_3$, upon which are running an outer electrode lead 21 and an $MO_x$ electrode lead 17. Understood by $MO_x$ in this context is a generally known mixed oxide of an inexactly defined stoichiometry such as $Ti_{0.95}Nb_{0.05}O_{2+x}$. Hot region 40 is initially covered by an $MO_x$ electrode 20.

Figure 2:
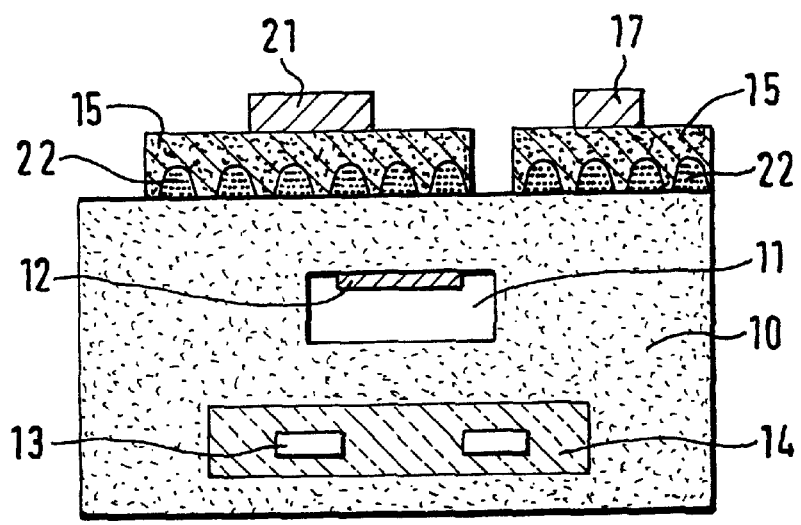
FIG. 2 shows a cross-section along line II, of FIG. 1, of a sensor for analyzing gases according to the present invention.

FIG. 2 shows FIG. 1 in the intersection along line II in cold region 30. Located in the interior of substrate 10 are a heater 13 having a surrounding heater insulation 14, a reference air channel 11 and a Pt reference electrode 12. Insulation layers 15 run continuously between electrode leads 17 and 21 and substrate 10. Insulation layers 15 and substrate 10 are joined by way of adhesion nubs 22.

Figure 3:
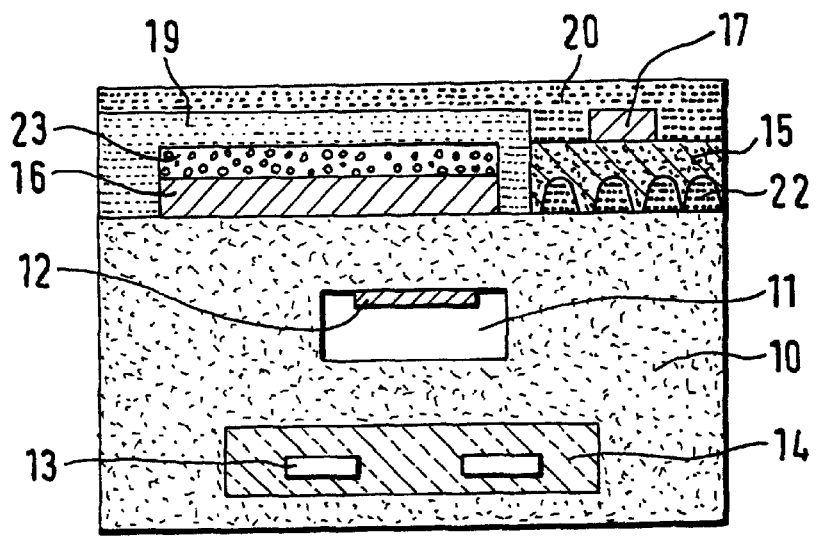
FIG. 3 shows another cross-section along line III, of FIG. 1, of a sensor for analyzing gases according to the present invention.

FIG. 3 shows FIG. 1 in the intersection along intersection line III in hot region 40. Running initially here on substrate 10 is outer electrode 16 as a Pt outer electrode which is contacted via outer electrode lead 21. A highly porous, gas-permeable tunnel layer 23 is also applied on outer electrode lead 21. For example, tunnel layer 23 is produced prior to the final sintering of the gas sensor in the green state by screen-printing a $ZrO_2$-containing layer onto outer electrode 16, which then during sintering becomes a highly porous, gas-permeable tunnel layer 23 made of $ZrO_2$, and which exhibits a markedly increased open porosity, particularly compared to electrolyte layer 19 disposed above it. Tunnel layer 23 and Pt outer electrode 16 are surrounded laterally and above by an electrolyte layer 19 made of dense or slightly porous $ZrO_2$. In addition to outer electrode 16, insulation layer 15 already present in cold region 30 is also extended here uninterrupted, upon which the likewise extended $MO_x$ electrode lead 17 runs. In this manner, $MO_x$ electrode lead 17 is continuously electrically separated from substrate 10 and electrolyte layer 19 in hot region 40, as well. Adhesion nubs 22 are likewise applied between insulation layer 15 and substrate 10.

In order to open up an access for the gas to be analyzed to tunnel layer 23 as simply as possible, tunnel layer 23 is constructed in a planar manner, such that at least region-wise in the direction of cold side 30 of gas sensor 5, it is not covered by $MO_x$ electrode 20 and electrolyte layer 19, so that the gas to be analyzed can reach Pt outer electrode 16 directly via tunnel layer 23 without having to diffuse through $MO_x$ electrode 20 and dense or slightly porous electrolyte layer 19 beforehand. In this manner, a planar gas-intake orifice 24 is formed which is in direct contact with the measuring gas and via which the gas to be analyzed can enter into tunnel layer 23.

A second exemplary embodiment provides for doping gas-permeable tunnel layer 23 with a catalytically active material. This can be carried out, for example, in a manner known per se, by an appropriate addition into the $ZrO_2$-containing layer, produced in the green state using a screen-printing method, analogous to the first exemplary embodiment. For example, a noble metal such as Pd, Rh or Pt, a noble-metal alloy or a transitional metal oxide such as a manganese oxide is suitable as catalytically active material. This catalytically active material is introduced, in particular, into the pores of the tunnel layer and has, for example, the form of nano-scale colloids.

A third exemplary embodiment, which is otherwise completely analogous to the first exemplary embodiment, provides for forming tunnel layer 23 as a diffusion barrier which is permeable to specific gases. Suitable for this purpose is, for example, a tunnel layer 23 composed of porous zircon dioxide or porous aluminum oxide.

In a further exemplary embodiment, tunnel layer 23 is formed as a self-supporting cavity.

What is claimed is:

1. A sensor for determining at least one of gas components and gas concentrations of a gas mixture in exhaust gases of an internal combustion engine, comprising:
    an outer analyzing electrode in communication with the gas mixture;
    an electrolyte layer in contact with the outer analyzing electrode;
    an $MO_x$ electrode separated from the outer analyzing electrode by the electrolyte layer and in communication with the gas mixture, wherein $MO_x$ is a mixed oxide;
    a substrate coupled to the outer analyzing electrode; and
    a gas-permeable tunnel layer having a region directly exposed to the gas mixture,
    wherein the outer analyzing electrode has a region in contact with the gas-permeable tunnel layer, allowing the gas mixture to be supplied via the gas-permeable tunnel layer to the outer analyzing electrode.

2. The sensor of claim 1, wherein the gas mixture includes HC, $NO_x$ and CO.

3. The sensor of claim 1, wherein the gas-permeable tunnel layer covers the outer analyzing electrode.

4. The sensor of claim 1, wherein the outer analyzing electrode is surrounded by at least one of the substrate and the electrolyte layer.

5. The sensor of claim 1, wherein the $MO_x$ electrode is directly exposed to the gas mixture.

6. The sensor of claim 1, wherein the $MO_x$ electrode covers the electrolyte layer.

7. The sensor of claim 1, wherein the gas-permeable tunnel layer includes a gas intake surface which is not covered by the electrolyte layer and is not covered by the $MO_x$ electrode.

8. The sensor of claim 1, wherein the gas-permeable tunnel layer includes $ZrO_2$.

9. The sensor of claim 1, wherein the gas-permeable tunnel layer is doped with a catalytically active material.

10. The sensor of claim 9, wherein the catalytically active material includes a noble metal, a noble-metal alloy and/or a transitional metal oxide.

11. The sensor of claim 10, wherein the transitional metal oxide includes a manganese oxide.

12. The sensor of claim 10, wherein the catalytically active material is present in pores contained in the gas-permeable tunnel layer.

13. The sensor of claim 11, wherein the gas-permeable tunnel layer is present as a diffusion barrier which is permeable to specific gases.

14. The sensor of claim 1, wherein the gas-permeable tunnel layer includes a cavity.

* * * * *

UNITED STATES PATENT AND TRADEMARK OFFICE
CERTIFICATE OF CORRECTION

PATENT NO. : 6,544,394 B1
DATED : April 8, 2003
INVENTOR(S) : Rainer Strohmaier et al.

It is certified that error appears in the above-identified patent and that said Letters Patent is hereby corrected as shown below:

Column 1,
Lines 39 and 40, -- "Thus, the tunnel layer can also be advantageously formed as a self-supporting cavity, as a layer having great open porosity, or as a layer which is permeable to specific gases. --

Signed and Sealed this

Third Day of August, 2004

JON W. DUDAS
*Acting Director of the United States Patent and Trademark Office*